United States Patent [19]
Spisak et al.

[11] Patent Number: 5,591,912
[45] Date of Patent: Jan. 7, 1997

[54] METHOD AND APPARATUS FOR INSPECTING CONDUITS

[75] Inventors: Michael J. Spisak, Venetia; Roy A. Nance, McMurray, both of Pa.

[73] Assignee: The United States of America as represented by the United States Department of Energy, Washington, D.C.

[21] Appl. No.: 402,219

[22] Filed: Mar. 10, 1995

[51] Int. Cl.⁶ .................................................. G01N 29/06
[52] U.S. Cl. ............................. 73/623; 73/598; 73/625; 73/628; 73/629
[58] Field of Search ............................ 73/598, 600, 622, 73/623, 625, 628, 641, 629; 376/252, 249

[56] References Cited

U.S. PATENT DOCUMENTS

| | | | |
|---|---|---|---|
| 3,552,191 | 1/1971 | Heseding | 73/625 |
| 3,584,504 | 6/1971 | Proctor | 73/623 |
| 3,646,805 | 3/1972 | Walters | 73/623 |
| 4,305,297 | 12/1981 | Ries et al. | 73/628 |
| 4,361,044 | 11/1982 | Kupperman et al. | 73/623 |
| 4,362,059 | 12/1982 | Zwyssig | 73/628 |
| 4,663,727 | 5/1987 | Saporito et al. | 73/623 |
| 4,856,337 | 8/1989 | Metala et al. | 73/623 |

FOREIGN PATENT DOCUMENTS

| | | | |
|---|---|---|---|
| 3425811 | 3/1985 | Germany | 73/623 |
| 523347 | 10/1974 | U.S.S.R. | 73/628 |

OTHER PUBLICATIONS

"Aerotech Transducers" (sales brochure), Krautkrammer Branson Ultransonic Transducer Catalog, p. 19.
Robert C. McMaster, "Nondestructive Testing Handbook", American Society for Nondestructive Testing Handbook, The Ronald Press Co., New York, 1959, vol. II, pp. 49.8–49.13.

*Primary Examiner*—Hezron E. Williams
*Assistant Examiner*—Nashmiya Ashraf
*Attorney, Agent, or Firm*—Virginia B. Caress; William R. Moser; Paul A. Gottlieb

[57] ABSTRACT

An apparatus and method for ultrasonic inspection of a conduit are provided. The method involves directing a first ultrasonic pulse at a particular area of the conduit at a first angle, receiving the reflected sound from the first ultrasonic pulse, substantially simultaneously or subsequently in very close time proximity directing a second ultrasonic pulse at said area of the conduit from a substantially different angle than said first angle, receiving the reflected sound from the second ultrasonic pulse, and comparing the received sounds to determine if there is a defect in that area of the conduit. The apparatus of the invention is suitable for carrying out the above-described method. The method and apparatus of the present invention provide the ability to distinguish between sounds reflected by defects in a conduit and sounds reflected by harmless deposits associated with the conduit.

1 Claim, 2 Drawing Sheets

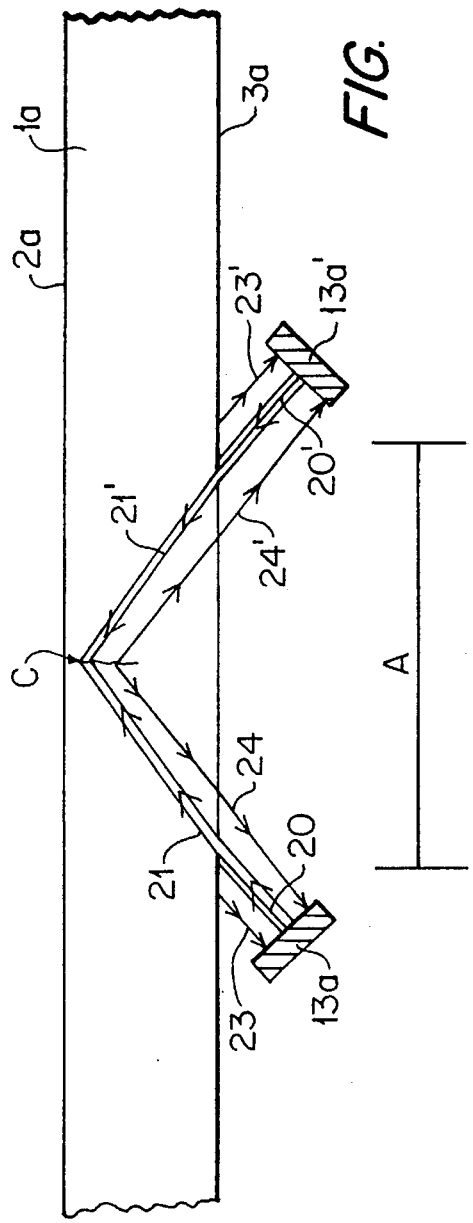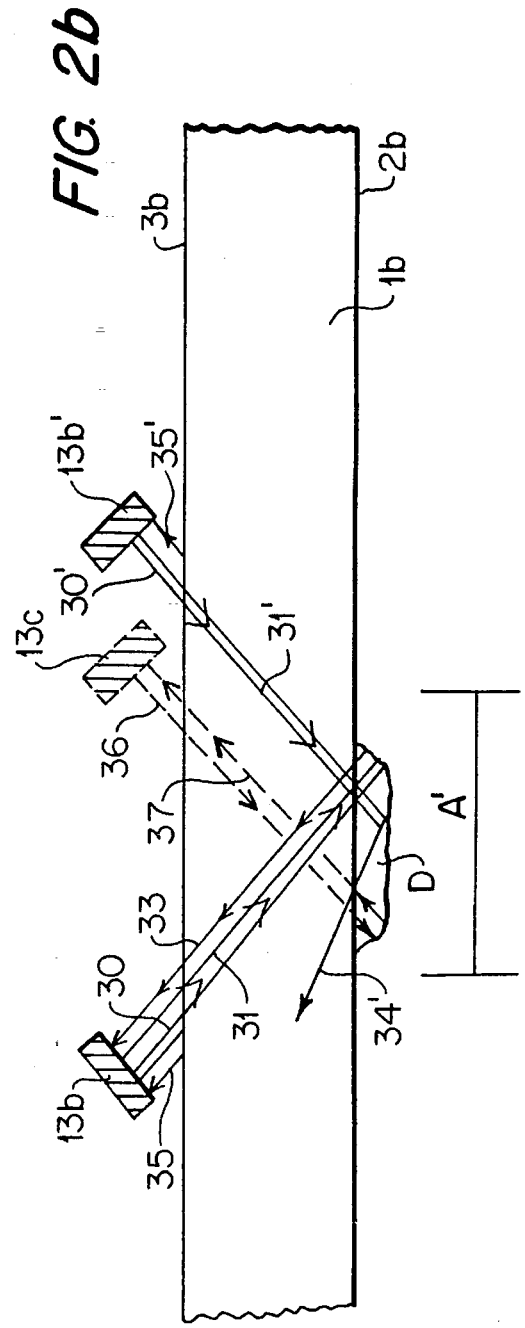

METHOD AND APPARATUS FOR INSPECTING CONDUITS

BACKGROUND OF THE INVENTION

1. Field of the Invention

The present invention is generally applicable to the ultrasonic inspection of conduits. More particularly, the inspection method and apparatus of the present invention permit differentiation between defects in conduits and deposits of foreign materials associated with conduits.

2. The Prior Art

Ultrasonic inspection probes useful in the inspection of conduits are known. Such probes generally contain multiple (typically eight) individual transceiver elements all pointing toward the conduit at the same general angle and equally spaced around the probe body, each of which inspects a particular section of the conduit. These probes are capable of detecting both simulated cracks and actual cracks produced in laboratory samples of tubing. An example of such a probe is the Aerotech boreside array transducer.

However, during the first extensive field use of such ultrasonic inspection probes, a large number of defect-like sounds were detected which could not be verified upon visual inspection of the conduit. It was subsequently determined that non-detrimental deposits of materials on the exterior of the conduits were producing these sounds.

The *Nondestructive Testing Handbook*, Vol. II, pp. 49.8–49.13, The Ronald Press Company, New York (1959) discloses a search unit employing separate transmit-receive search units in a so-called, "pitch-catch" relationship. However, this arrangement would not provide sufficient information to distinguish defects from deposits of materials on the exterior of the conduit since the sound is only directed from one direction.

The ultrasonic sound reflected by a defect and the sound reflected by a deposit produce electronic signal responses which appear very similar. Thus, in many instances, a deposit is indistinguishable from a defect. Accordingly, there is a need for improvement in the means and methods employed for inspecting such conduits in order to avoid unnecessary repair or replacement of conduits which contain no defects.

SUMMARY OF THE INVENTION

Therefore, it is the primary object of the present invention to provide a method for ultrasonic inspection of conduits which allows sound reflected from defects in the conduits to be distinguished from sounds reflected from deposits of material associated with the conduits.

It is a still further object of the present invention to provide an apparatus which can be employed in the improved method of the present invention.

It is a still further object of the present invention to provide a method for processing the sounds from ultrasonic probes which provides a clear way of distinguishing defects in conduits from deposits associated therewith.

In a first aspect, the present invention relates to a method for the ultrasonic inspection of an area of a conduit. The first step of the method involves directing a first ultrasonic pulse, from a probe positioned inside a conduit, at a particular area of a conduit at a first angle. Then, the reflected sound from the ultrasonic pulse is received from the area of the conduit. Almost simultaneously of subsequently within a fraction of a second (typically $6\times10^{-5}$ sec.) while the probe is substantially in the same location, a second ultrasonic pulse is directed at the same area of the conduit from a substantially different angle, i.e. from an opposing direction, from said first angle and the reflected sound from the second ultrasonic pulse is then received from that area of the conduit. Finally, the received sounds are compared to determine if there is a defect in that area of the conduit. Since the method of the present invention provides two pieces of information obtained from different angles about each area of the conduit, it is possible to distinguish reflected sounds indicative of a defect in the conduit from reflected sounds indicative of a deposit associated with the conduit.

The present invention also relates to a method for the ultrasonic inspection of a conduit, which method employs the same steps as the method above and additionally requires that a new area of the conduit be chosen which is incrementally displaced from the previously inspected area and that the above-described method, including the step of choosing a new area of the conduit, be repeated until the inspection of the conduit is completed.

In yet another embodiment, the present invention relates to an apparatus for use in the ultrasonic inspection of conduits. The apparatus includes a probe body which is adapted for travel within a conduit. In addition, the apparatus includes at least one pair of first and second ultrasonic transceivers positioned at different points along the length of the probe body for directing ultrasonic pulses at a common area of a conduit from substantially different angles relative thereto and for receiving sound reflected from the conduit, and including means for comparing the sounds received by the transceivers in order to locate any defect in said area of the conduit.

The primary advantage of the methods and the apparatus of the present invention is that they allow sounds reflected from defects in the conduit to be distinguished from sounds reflected by deposits of material associated with the conduit. In this manner, replacement and/or dismantling of apparatus having non-detrimental deposits and no defects can be avoided since the sounds reflected by deposits can be distinguished and disregarded. This represents a substantial improvement over the prior art device and methods which were incapable of distinguishing defects from deposits.

Other objects, features and advantages of the present invention will be set forth or apparent from the description of the preferred embodiments which follows.

BRIEF DESCRIPTION OF THE DRAWINGS

FIG. 2a is a schematic representation of the path of the ultrasonic pulses from transceivers and the reflected sound produced when these ultrasonic pulses impinge upon a defect in a conduit.

FIG. 2b is a schematic representation of the path of the ultrasonic pulses from transceivers and the reflected sound produced when these ultrasonic pulses impinge upon a deposit on the exterior surface of a conduit.

DETAILED DESCRIPTION OF THE PREFERRED EMBODIMENTS

Figure 1:
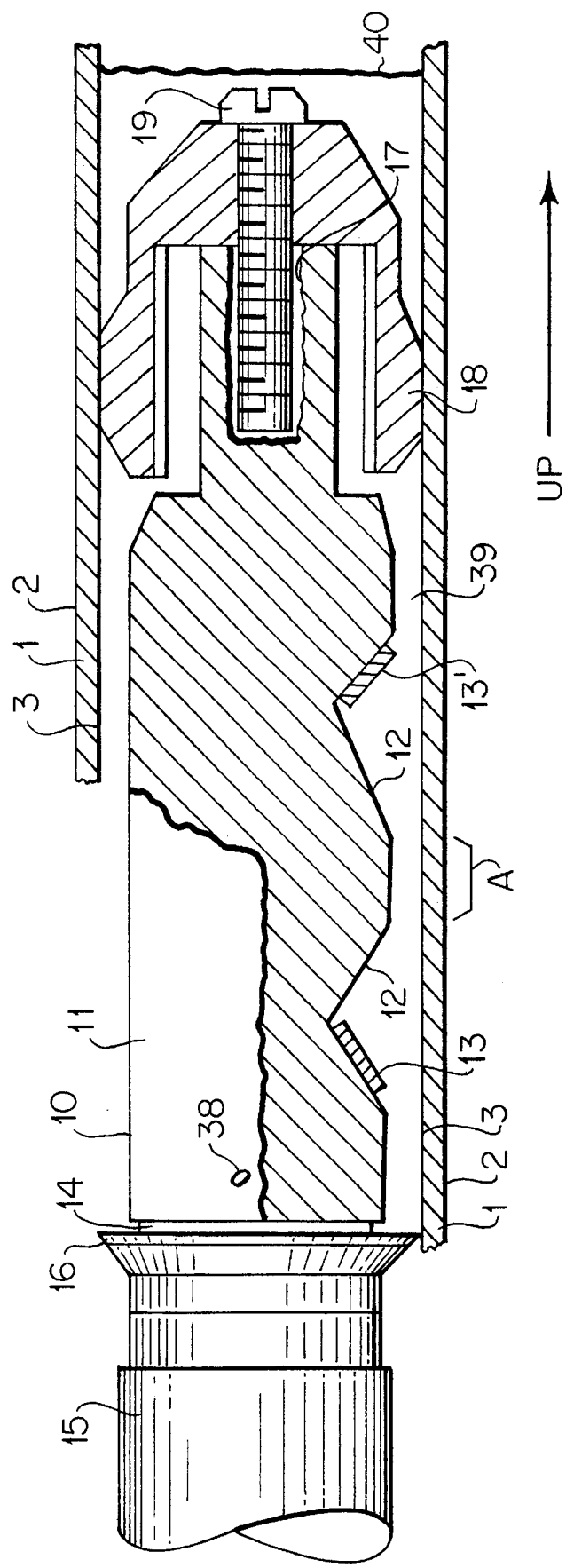
FIG. 1 is a partial cross-sectional view of an ultrasonic probe in accordance with the present invention located inside of a conduit.

Referring now to the figures, like elements are represented by like numerals throughout the several views.

Referring to FIG. 1, there is shown a conduit 1 having an outer surface 2 and an inner surface 3. The conduit 1, which is cylindrical in shape, is shown in longitudinal cross-section in this figure. For the purpose of this figure, area A is the area of the conduit being inspected.

Also shown in FIG. 1 is a probe 10, which is depicted in partial cross-section. The probe 10 includes a probe body 11 comprising indentations 12 therein. In indentations 12 are mounted transceiver elements 13 and 13'. For ease of manufacture, it is preferred that transceiver elements 13 and 13' are mounted in a fixed position on probe body 11. However, it is possible to mount transceiver elements 13 and 13' in a manner whereby their angular direction can be adjusted, if desired.

On the left-hand side of FIG. 1, the front of the probe 10 is shown. Preferably, the front of probe 10 includes a connecting means 14 which may be, for example, a threaded tube. Connecting means 14 is adapted for connection to a means for pulling the probe 10 through the conduit. In the embodiment of FIG. 1, the means for pulling the probe through the conduit includes a nylon wand 15 and a water seal 16 which is adapted to maintain water 39, or other appropriate liquid necessary for transmission of the sound from the transceivers 13 and 13' into the conduit 1, in the region of the probe body 11 with a water level 40 above the transceivers 13 and 13' and elements associated therewith when the probe 10 is used to inspect a nominally vertically oriented conduit 1. A second water seal (not shown) can be added near the centering guide 18 to capture water in the subject region when the probe 10 is used to inspect conduit 1 in other than vertical (e.g. nominally horizontal) orientations.

On the right hand side of FIG. 1 is shown the rear end of probe 10. The rear end of probe 10 may include a threaded aperture 17 which is adapted for attachment of a centering guide 18 by screw means 19 to the rear end of probe body 11. Centering guide 18 functions to maintain the probe body 11 centered in the conduit 1 such that the distance between the transceivers 13 and the walls of conduit 1 remains essentially constant. One or more water ports 38 are provided in the probe body 11 to conduct the water into the region of transceivers 13 and 13'. The water 39 is supplied to the probe body 11 through the hollow wand 15 which also contains the signal carrying wires between the transceivers 13 and 13' and the electronic instrumentation which activates the transceivers 13 and 13' and process the signals.

In operation for the inspection of a specific area A of conduit 1, a first ultrasonic pulse is directed at area A from the forward transceiver 13 and a second ultrasonic pulse is directed almost simultaneously or subsequently at the same area A of conduit 1 from the rear transceiver 13'. Transceivers 13 and 13' are located at a known distance from conduit 1 since centering guide 18 maintains transceivers 13 and 13' at a relatively constant distance from the inner surface 3 of conduit 1. Further, the angle at which transceivers 13 and 13' are positioned on probe body 11 is also known such that the distance between transceivers 13 and 13' and area A can be calculated.

The ultrasonic pulses from transceivers 13 and 13' will impact inner surface 3 of conduit 1 whereby a portion of the sound will reflect back to the transceivers 13 and 13', respectively. Thus, the probe 10 of the present invention will always record a baseline sound which indicates the position of the inner surface 3 of conduit 1.

The ultrasonic pulse continues, in part, through the walls of conduits 1 and, assuming that there are no defects in conduit 1, essentially no further sound will be reflected back to transceivers 13 and 13'. However, if there is a crack in conduit 1, a further portion of the ultrasonic pulse will reflect back to transceivers 13 and 13' as a second reflected sound. In addition, deposits located on outer surface 2 of conduit 1 can also result in the reflection of a portion of the ultrasonic pulse back to transceivers 13 and 13' as a reflected sound with resembles the sound indicative of a defect in the conduit. Since most deposits on outer surface 2 of conduit 1 are non-detrimental, it is necessary to be able to distinguish reflected sounds from deposits on outer surface 2 from reflected sounds from cracks or other defects in conduit 1.

Referring now to FIGS. 2a–2b, there is shown the principle of the present invention which allows reflected sounds from defects to be distinguished from reflected sounds from deposits. In FIG. 2a is shown conduit 1a having outer surface 2a and inner surface 3a. The probe 10 is not shown in this figure, but the approximate location of transceivers 13a and 13a' during inspection is shown. FIG. 2a depicts the pattern of travel of ultrasonic pulses in the case of a crack C in conduit 1a.

As can be seen, the transceivers 13a and 13a' each emit an ultrasonic pulse 20 and 20', part of which passes through inner surface 3a of conduit 1a and continues on as ultrasonic pulses 21 and 21' until they reach crack C. When ultrasonic pulses 20 and 20' impinge on inner surface 3a of conduit 1a, portions of ultrasonic pulses 20 and 20' are reflected back to transceivers 13a and 13a' as reflected sound 23 and 23'. Further, when ultrasonic pulses 21 and 21' impinge on crack C, part of ultrasonic pulses 21 and 21' are reflected back as reflected sound 24 and 24' to transceivers 13a and 13a'.

Thus, reflected sound 23 and 23' provide a baseline indicative of the position of inner surface 3a of conduit 1a. Further, reflected sound 24 and 24' from crack C are indicative of the position and existence of crack C. It is important to note that if transceivers 13a and 13a' are substantially equidistant from inspection area A, then there will be some overlap in the pattern produced by reflected sound 24 and 24' from crack C when the reflected sounds received at transceivers 13a and 13a' are plotted versus time and laid over one another. This is apparent from FIG. 2a since at the instant that crack C is centered between transceivers 13a and 13a', the reflected 24 and 24' will travel an equal distance and thereby will arrive back at transceivers 13a and 13a' with nominally the same time interval. Thus, a crack will produce a distinct signal for both transceivers 13a and 13a' at nominally the same moment in time, when centered between the transceivers 13a and 13a'.

When transceivers 13a and 13a' are not positioned equidistant from inspection area A or are not inspecting the same inspection area A at the same time, it is still possible to compare the reflected sounds for a given inspection area A by isolating the reflected sounds for that inspection area, plotting them versus time and laying them over one another to determine if the reflected sounds overlap or not. If there is an overlap this would be indicative of a defect in the conduit 1. Referring now to FIG. 2b, there is depicted the paths of sound travel in the case of a deposit D. As before, each of transceivers 13b and 13b' emit ultrasonic pulses 30 and 30' which impinge on inner surface 3b of conduit 1b at which point a portion of pulses 30 and 30' continue on as pulses 31 and 31' through the wall of conduit 1b until they impinge upon deposit D. Of course, a portion of each ultrasonic pulse 30 and 30' is reflected back by the inner surface 3b of the conduit 1b to transceivers 13b and 13b' as reflected sound 35 and 35'.

When pulse 31 from transceiver 13b reaches deposit D, it impinges on a surface of deposit D which is properly oriented to reflect sound back to transceiver 13b and thus the pulse is reflected back as reflected sound 33. Reflected sound 33 received at transceiver 13b is indicative of the location and existence of a deposit D.

Pulse 31' from transceiver 13b', however, will impinge upon a different surface of deposit D whereby the pulse 31' will be reflected as reflected sound 34'. However, reflected sound 34' does not return to transceiver 13b', but rather is reflected in a different direction. Thus, the deposit D will reflect no sound back to transceiver 13b' when it is located in the position shown in FIG. 2b. Accordingly, when the two plots of reflected sound versus time are overlaid for this inspection area A, there will be no overlapping reflected sound as there was above with respect to a crack C in FIG. 2a.

When transceiver 13b' is displaced to a position indicated by transceiver 13c and thus is in the process of inspecting a different inspection area A', then the pulse 36 from transceiver 13c will impinge upon a surface of the deposit D which is properly oriented to reflect back reflected sound 37 to transceiver 13c. Accordingly, at this point in time there will be sound reflected by the deposit D to transceiver 13c for inspection area A'. However, since transceiver 13b is also displaced from its original location at this time, it would not receive any reflected sound from the deposit D since it would no longer be aligned with the surface of deposit D which was properly oriented to reflect sound back at transceiver 13b. Thus, when the plots of the reflected sound versus time are overlaid, again there will be no overlapping sound since one of the transceivers 13b and 13c will not be receiving reflected sound for this inspection area A'.

Accordingly, from FIGS. 2a–2b it can be seen that the reflected sound generated by a crack can be distinguished from the reflected sound generated by a deposit since reflected sound generated by a crack will generally be received at both transceivers 13 and 13' for a given inspection area A, whereas a deposit will generally produce reflected sounds for transceivers 13 and 13' in two different inspection areas A and A' along conduit 1 whereby the signal from a crack can be distinguished from a deposit by overlaying the plots of reflected sound versus time for a given inspection area.

In actual practice, it is a good idea to choose inspection areas such that there is some overlap between adjacent inspection areas. This will generally provide several matched pairs of reflected sounds for a given defect since the defect will be within several different overlapping inspection areas. This will, in turn, provide an additional check on the inspection to thereby reduce the chance of error. In this case, deposits will also produce several reflected sounds but generally several of these reflected sounds will appear singly in different inspection areas rather than as matched pairs in the same inspection areas such that deposits can be even more reliably distinguished from defects in this manner.

The present invention also relates to a method for the inspection of entire lengths of conduit. This method involves the same steps as the above-described method except that after a particular area A of conduit 1 has been inspected, a new area A' incrementally displaced from original inspection area A is chosen for inspection and the same method steps are repeated for new inspection area A'. This process is continued until the entire length of conduit 1 has been inspected. Typically, this is carried out by slowly pulling probe 10 through conduit 1 while at the same time emitting periodic ultrasonic pulses from probe 10. In this manner, each ultrasonic pulse is emitted at a different point in conduit 1, thereby providing results from different inspection areas.

The reflected sounds received by transceivers 13 and 13' may be plotted versus time whereby the reflected sounds at the beginning of the graph will correspond to the beginning of the conduit 1. Such reflected sound plots include a solid baseline indicative of the inner surface 3 of conduit 1 and additional reflected sounds to the right of the baseline which are indicative of defects or deposits. The distance from left to right on the graph is indicative of the distance that the ultrasonic pulse 20 must travel before the reflected sound returns to transceivers 13 and 13'. Thus, the baseline created by reflected sound 23 will be to the left of the reflected sound for a crack C since the inner surface 3 of conduit 1 is closer to transceivers 13 and 13' than is crack C.

It is possible to further process the reflected sounds to provide a more accurate picture of the conduit 1. For example, ultrasonic imaging may be employed in order to provide so-called A-scans, which are essentially a composite, 3-dimensional view of the sounds received by transceivers 13a and 13a'. Such A-scans can be generated by known methods and known means for ultrasonic imaging.

Finally, an additional step in the analysis could be to make a plan view of the data by digitizing each A-scan and color coding the various reflected sound amplitudes. This can be helpful to precisely locate crack C in conduit 1 since the amplitude of the reflected sound is indicative of the exact location of the crack. Further, such data processing techniques can enhance the ability of the operator of the device to distinguish between noise and reflected sounds produced by defects in the conduit.

The distance between transceivers 13 and 13' and the inspection area A is important. In the preferred embodiment, which provides the most simplicity, transceivers 13 and 13' are positioned equidistant from inspection area A as shown in the figures such that the distance between transceivers 13 and 13' and the inspection area A cancels out. However, it is possible to position transceivers 13 and 13' at different distances from inspection area A. In this case, it will be necessary to correct for these differences in distance when comparing and/or processing the reflected sound received by transceivers 13 and 13'.

It is also possible to inspect different areas A of the conduit 1 at the same time, as long as each of the transceivers 13 and 13' direct an ultrasonic pulse at each inspection area A at some point during the inspection. In this embodiment, a correction of the reflected sound output will be necessary in order to efficiently compare the reflected sounds since, for example, transceiver 13a would inspect inspection area A at a later time than transceiver 13a'.

In an even more advantageous embodiment, probe 10 will include multiple pairs of transceivers 13 spaced circumferentially about probe body 11 that are sequentially pulsed by a multiplexing electronic circuit at a very high rate (typically at a 10 kiloHertz rate) such that the probe 10 can inspect the conduit 1 in many radial paths essentially simultaneously. Depending on the transceiver element size and the number of transceivers 13 chosen it would be possible to inspect the entire conduit 1 in a single pass.

The foregoing detailed description of the invention has been provided for the purpose of illustration and description only and is not to be construed as limiting the invention in any way. The scope of the invention is to be determined by the claims appended hereto.

What is claimed is:

1. An ultrasonic inspection method of inspecting an area of a conduit to detect a defect or a deposit, which comprises the steps of:

a) positioning a probe inside said conduit, said probe comprising a pair of ultrasonic transceivers positioned on said probe such that said transceivers are on either side of and substantially equidistant from said area;

b) directing a first ultrasonic pulse, from a first transceiver of said pair, at said area of the conduit, from a first direction axially forward of said area; and substantially simultaneously directing a second ultrasonic pulse, from a second transceiver of said pair, at said area of the conduit, from a second direction axially rearward of said area;

c) receiving at said first transceiver reflected sound signals caused by reflection of said first ultrasonic pulse from said area;

d) receiving at said second transceiver reflected sound signals caused by reflection of said second ultrasonic pulse from said area;

e) plotting said reflected sound signals versus time, wherein a defect is distinguished from a deposit and identified by observing overlap of signal patterns produced by both said transceivers, indicating that said reflected sound is received at the same time by both said transceivers.

* * * * *